United States Patent [19]
Porter et al.

[11] Patent Number: 5,307,146
[45] Date of Patent: Apr. 26, 1994

[54] DUAL-WAVELENGTH PHOTOMETER AND FIBER OPTIC SENSOR PROBE

[75] Inventors: Marc D. Porter, Ames, Iowa; Thomas P. Jones, Waukesha, Wis.; Shelley J. Coldiron, Ames, Iowa

[73] Assignee: Iowa State University Research Foundation, Inc., Ames, Iowa

[21] Appl. No.: 962,394

[22] Filed: Oct. 16, 1992

Related U.S. Application Data

[63] Continuation-in-part of Ser. No. 761,684, Sep. 18, 1991, abandoned.

[51] Int. Cl.$^5$ .................... G01J 3/427; G01N 21/31
[52] U.S. Cl. .................... 356/320; 250/227.23; 356/408; 356/410; 356/411; 356/412; 356/434; 356/435
[58] Field of Search ............... 356/320, 408, 409, 410, 356/411, 412, 425, 434, 435; 250/227.18, 227.23

[56] References Cited

U.S. PATENT DOCUMENTS

| | | | |
|---|---|---|---|
| 4,213,677 | 7/1980 | Sugimoto et al. | 385/34 |
| 4,278,762 | 7/1981 | Svendsen | 435/13 |
| 4,281,245 | 7/1981 | Brogardh et al. | |
| 4,342,919 | 8/1982 | Brogardh | 250/577 |
| 4,582,589 | 4/1986 | Ushizawa et al. | 204/433 |
| 4,596,925 | 6/1986 | Gilby | |
| 4,637,730 | 1/1987 | Ponstingl et al. | 356/41 |
| 4,644,154 | 2/1987 | Brogardh et al. | |
| 4,678,904 | 7/1987 | Saaski et al. | 250/226 X |
| 4,683,374 | 7/1987 | Weiss | |
| 4,778,987 | 10/1988 | Saaski et al. | 250/226 |
| 4,803,049 | 2/1989 | Hirschfeld et al. | 422/58 |
| 4,814,604 | 3/1989 | Lequime | 356/367 X |
| 4,907,857 | 3/1990 | Guiliani et al. | 250/227.23 |
| 4,920,056 | 4/1990 | Dasgupta | 436/50 |
| 4,983,824 | 1/1991 | Saaski et al. | 250/227.27 |
| 5,021,731 | 6/1991 | Saaski et al. | 324/96 |
| 5,039,491 | 8/1991 | Saaski et al. | 422/82.05 |
| 5,039,492 | 8/1991 | Saaski et al. | 422/82.09 |
| 5,094,958 | 3/1992 | Klainer et al. | 356/408 |

FOREIGN PATENT DOCUMENTS

127476A2  5/1984  European Pat. Off. .

OTHER PUBLICATIONS

Hermann E. Posch and Otto S. Wolfbeis, "Optical and Fibre-Optic Sensors for Vapours of Polar Solvents," Talanta, vol. 35, No. 2, pp. 89–94 (1988).

A. J. Guthrie et al., "Solid-State Instrumentation for Use with Optical-Fibre Chemical-Sensors," Talanta, vol. 35, No. 2, pp. 157–159 (1988).

Richard R. Smardzewski, "Multi-Element Optical Waveguide Sensor: General Concept and Design," Talanta, vol. 35, No. 2, pp. 95–101 (1988).

(List continued on next page.)

Primary Examiner—Vincent P. McGraw
Attorney, Agent, or Firm—Leydig, Voit & Mayer

[57] ABSTRACT

A dual wavelength optical sensor for measuring chemical properties of a particular quantity, the optical sensor including a sensor probe having a thin sensing film whose optical characteristics are responsive to the chemical properties of the measured quantity at at least two distinct wavelengths of light in such a way that when the responses to the at least two distinct wavelengths are combined, a self-calibrated measurement of the measured chemical property is provided. A light source generates the at least two distinct wavelengths of light, and a single optical fiber carries the light from the light source to the sensor probe. A sample detector receives the light from the sensor probe after it has passed to and from the thin sensing film and produces light intensity readings for the at least two distinct wavelengths of light. The optical sensor also includes a signal processing system for combining the light intensity readings from the sample detector to produce the self-calibrated measurement which accounts for changes in the optical characteristics of the thin sensing film that otherwise contribute to instability in the sensor response.

34 Claims, 9 Drawing Sheets

U.S. PATENT DOCUMENTS

J. F. Giuliani et al., "Reversible Optical Waveguide Sensor for Ammonia Vapors," Optics Letters, vol. 8, No. 1, pp. 54-56 (Jan. 1983).

J. E. Freeman et al., "A Fibre-Optic Absorption Cell for Remote Determination of Copper in Industrial Electroplating Baths," Analytica Chimica Acta, 177, pp. 121-128 (1985).

H. Kopola et al., "An Eight Channel Fibre Optical Spectrophotometer for Industrial Applications," SPIE vol. 586, Fiber Optic Sensors, pp. 204-210 (1985).

Thomas P. Jones and Marc D. Porter, "Optical pH Sensor Based on the Chemical Modification of a Porous Polymer Film," Analytical Chemistry, vol. 60, No. 5, pp. 404-406 (Mar. 1988).

Research International, "ChemCard 2000 TM", undated brochure.

Research International, "pH monitor", undated brochure.

R. A. Lieberman and G. E. Blonder, AT&T Bell Laboratories, "An Improved Interferometric Pressure Optrode", SPIE vol. 838, Fiber Optics and Laser Sensors V (1987), pp. 49-59.

A. L. Harmer, Battelle, Geneva Research Centres, Switzerland, "Principles of Optical Fibre Sensors and Instrumentation", Measurement and Control, vol. 15, pp. 143-151 (Apr. 1982).

Kazuo Kyuma, Shbichi Tai. and Masahiro Nunoshita, Central Research Laboratory, Mitsubishi Electric Corporation, "Development of Fibre Optic Sensing Systems—A Review", Optic and Lasers in Engineering, pp. 155-182 (1982).

W. Rudolf Seitz, Department of Chemistry, University of New Hampshire, "Chemical Sensors Based on Fiber Optics", Analytical Chemistry, vol. 45, No. 1, pp. 16A-34A (Jan. 1984).

MetriCor (Brochure), Display & Control, Fiberoptic MultiSensor System, Model 1400, undated.

Elric W. Sasaki, James C. Hartl, and Gordon L. Mitchell, MetriCor, "A Fiber Optic Sensing Systems Based On Spectral Modulation", Instrument Society of America, Advances in Instrumentation, vol. 41, Part 3, pp. 1177-1184 (1986).

○ ABSORBANCE AT 635 nm
● ABSORBANCE AT 565 nm

DUAL-WAVELENGTH PHOTOMETER AND FIBER OPTIC SENSOR PROBE

The United States Government has certain rights in this invention pursuant to Contract No. ITA87-02 between the U.S. Department of Commerce and Iowa State University.

CROSS-REFERENCE TO RELATED APPLICATIONS

This is a continuation-in-part of U.S. patent application Ser. No. 761,684, filed Sep. 18, 1991 now abandoned.

FIELD OF THE INVENTION

The present invention relates to optical sensors, and more particularly, to optical sensors used to measure the optical properties of thin sensing films which are responsive to particular physical quantities to be measured.

BACKGROUND OF THE INVENTION

Thin film optical sensors have been used based on an optical sensor measuring changes in a thin sensing film for detecting and measuring physical quantities such as pH, metal-ion, and toxic gas levels. While different optical sensors exist, certain optical sensors include the use of a photometer, which is a device used to measure the optical properties of a thin film which is responsive to a particular physical characteristic or quantity to be measured. In other words, the optical properties of the thin sensing film are responsive to the chemical properties of the physical quantities being measured. For example, the thin film can be responsive to pH, and changes in the optical properties of the film resulting from changes in the pH level are measured by the photometer whose output is calibrated in terms of pH.

Important application areas for such sensors can be found in environmental and clinical applications where there is a need for reliable, low-cost and portable sensors. However, due at least in part to the complexities of realizing analytical instrumentation to meet the demands of the above applications, the foregoing need has not been adequately satisfied. Indeed, only few reports describing such instrumentation have appeared, such as R. Smardzewski, "Multi-Element Optical Waveguide Sensor: General Concept and Design", Talanta, Vol. 35, No. 2, pp. 95-101 (1988), and A. Guthrie et al., "Solid-State Instrumentation For Use With Optical-Fibre Chemical-Sensors", Talanta, Vol. 35, No. 2, pp. 157-159 (1988).

An important focus of the prior attempts has been the provision of low-cost, solid state components for the optical sensor portion of the instrument, which have included the use of light emitting diodes (LEDS) as light sources and photodiodes as detectors. The LED has an additional advantage of producing light at only single defined wavelengths although at variable intensities. In the Smardzewski article cited above, for example, a multi-element optical waveguide sensor for detection and identification of gaseous or liquid mixtures was disclosed. For each component or element to be detected and measured, an optical waveguide such as a cylindrical glass capillary tube was provided. Each optical waveguide was externally coated with a thin film known to react specifically with the particular element to be detected. An LED was then attached to each waveguide, and each waveguide was fiber-coupled to a single photodetector, so that the photodetector provided an output indicative of the level of the element being detected. As is apparent, this sensor operated in a single-wavelength mode, i.e., a single LED provided a light output at a particular wavelength for each waveguide. However, optical sensors such as these which operate in a single-wavelength mode experience calibration problems, due in part to variations in the LED output intensity due to time, temperature, and life of the LEDS, and the degradation of the sensing films. As would be expected, these calibration problems lead to inaccuracy and instability in the sensor response.

In addition to optical sensors utilizing single-wavelength mode operation, two-wavelength schemes have been developed. For example, in the Guthrie et al. article cited above, a two-wavelength scheme was employed. There, an optical fiber pH sensor was incorporated with a solid state instrument including two LEDs and a photodiode detector. One LED provided a measuring wavelength, while the second LED provided a near-infrared "reference wavelength". The respective wavelengths of light were transmitted to a sensor probe on separate optical fibers and the signal intensity was measured at each wavelength by the single detector. Because the light emitted at the reference wavelength was not absorbed by the indicator reagent of the sensor probe, the reflected light intensity at the reference wavelength was independent of indicator state. The signal intensities at the measuring and reference wavelengths were then divided in order to provide a measurement dependent only on the indicator state. Thus, the reference wavelength was utilized to compensate for changes in the signal intensity due to non-chemical causes, such as fiber-bending intensity losses or intensity changes at the fiber connections. However, similar to single-wavelength mode sensors, this two-wavelength device used two completely independent optical sources for illuminating the sensor, and did not compensate for variations in the LED output intensities due to time, temperature, and life of the LEDS, or for variations due to degradation of the sensing film.

In addition to light source output fluctuations, the optical properties of the thin sensing films such as the concentration of the indicator, and the ability of the films to sense the measured physical quantities can change over time resulting in degradation of the sensing films, which further contributes to long-range stability problems. Attempts have been made to combat the long-term stability problems with respect to the optical characteristics of thin sensing films by, for example, regenerating the reagent associated with the film, using controlled release films, and the like. However, none of these techniques have provided optical sensing devices with the desired long-term stability and minimal recalibration requirements.

Another problem not fully addressed by prior developments is that many of the targeted applications demand extreme miniaturization of both the optical and electrical components of the optical sensors. Furthermore, in instances where implantation into a biological host is required for measuring physiological parameters such as blood pH, sodium, potassium, or calcium, biocompatibility of the optical sensor components is of considerable importance. Thus, as is apparent, the development of reliable, low-cost, and long-term optical sensors for environmental and clinical applications has not yet been achieved by the previous developments discussed above.

SUMMARY OF THE INVENTION

In view of the foregoing, it is a general aim of the present invention is to provide an optical sensor which is not only reliable, but which maintains long-term calibration far longer than sensors proposed in the past.

In accomplishing that aim, it is a primary object of the present invention to provide an optical sensor which has long-term stability and requires no recalibration after initial setup.

In that regard, it is another object of the present invention to provide an optical sensor which compensates for variations in the light source output intensities which cause instability and calibration problems.

It is a related object of the present invention to provide an optical sensor which also compensates and accounts for changes in the optical properties of the thin sensing films such as changes in the indicator concentration, or the ability of the films to sense the measured physical quantities, which contribute to the instability of the sensor response.

It is still another object of the present invention to provide an optical sensor which can be used in applications where the sensor probe of the optical sensor is inaccessible for recalibration or regeneration, such as in a biological host or underground.

In its broadest aspects, the present invention is directed to a dual wavelength optical sensor for measuring chemical properties of a particular quantity. The optical sensor of the present invention includes a sensor probe having a thin sensing film whose optical characteristics are responsive to the chemical properties of the measured quantity at at least two distinct wavelengths of light in such a way that when the responses to the at least two distinct wavelengths of light are combined, a self-calibrated measurement of the measured chemical property is provided. A light source generates the at least two distinct wavelengths of light, and a single optical fiber carries the light from the light source to the sensor probe. Sample detecting means are provided which receive the light from the sensor probe after it has passed to and from the thin sensing film and produce light intensity readings for the at least two distinct wavelengths of light. The optical sensor of the present invention also includes output means for combining the light intensity readings from the sample detecting means to produce the self-calibrated measurement which accounts for changes in the optical characteristics of the thin sensing film that otherwise contribute to instability in the sensor response.

In one specific embodiment encompassed within the broader aspects of the invention, the dual wavelength optical sensor includes light source means for producing light at two distinct wavelengths. For example, the light source means in this embodiment comprise two LEDS, each generating light at one of the respective wavelengths. A time-shared optical fiber receives the two distinct wavelengths of light from the light source means and carries the two distinct wavelengths on a time-shared basis to the thin sensing film of the sensor probe.

In a second specific embodiment also encompassed within the broader aspects of the present invention, the light source means comprise a wide spectrum light source which generates multiple wavelength light over a wide spectral range, with the at least two distinct wavelengths of light encompassed within this wide spectral range. In this second embodiment, the wide spectrum light produced by the light source means is carried to the sensor probe through a single optical fiber, where it is conveyed to and from the thin sensing film.

In both embodiments of the present invention, sample detecting means receive the light from the sensor probe after it has passed to and from the thin sensing film and produce light intensity readings at the respective wavelengths of light to which the thin sensing film responds. Output means combine the light intensity readings from the sample detecting means to produce the self-calibrated measurement which accounts for changes in the optical characteristics of the thin sensing film that otherwise contribute to instability in the sensor response. Additionally, reference detecting means sample the same light conveyed to the thin sensing film for providing compensation to the readings produced by the sample detecting means with respect to spectral variances in the output intensity of the light source means.

DETAILED DESCRIPTION OF THE PREFERRED EMBODIMENTS

While the invention will be described in connection with preferred embodiments, there is no intent to limit the invention to these embodiment. On the contrary, the intent is to cover all alternatives, modifications, and equivalents included within the spirit and scope of the invention as defined in the appended claims.

Figure 1A:
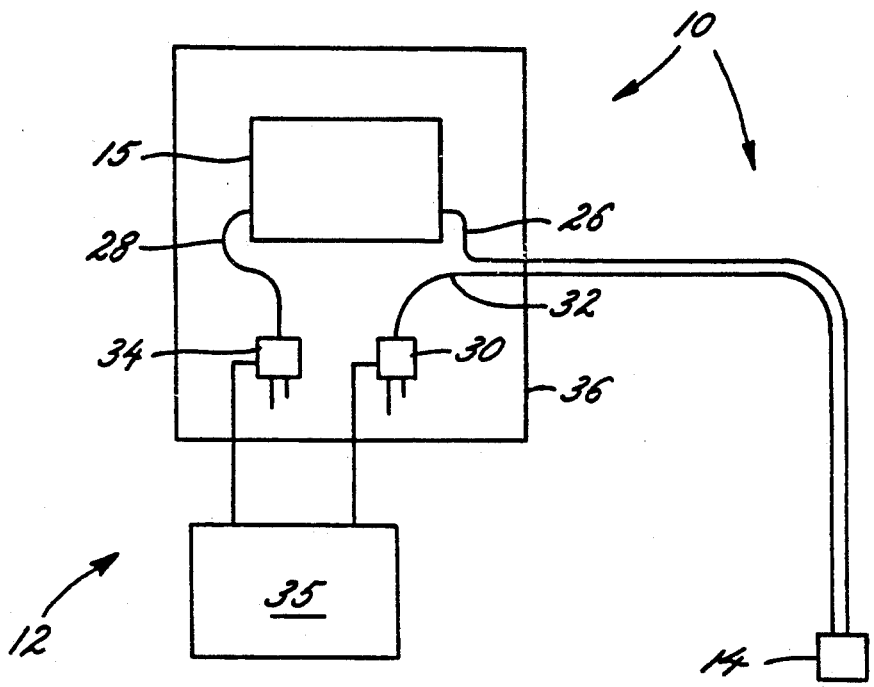
FIG. 1A is a block diagram of the dual wavelength optical sensor according to the present invention.

Turning now to the drawings, FIG. 1A is a block diagram of a dual wavelength optical sensor 10 according to the present invention. The optical sensor 10 is capable of providing a continuously calibrated measurement of the optical absorption of thin sensing films which are in turn responsive to a quantity to be measured, such as PH, metal-ion, or toxic gas levels, and physiological parameters such as blood pH, sodium, potassium, or calcium. While various implementations can be utilized to accomplish the inventive aspects described in the present application such as the two specific embodiments described below in connection with FIGS. 1B and 1C, in its broadest aspects, the present invention comprises a dual-wavelength photometer and fiber optic sensor probe as shown in FIG. 1A. A photometer 12 measures the optical characteristics of a thin sensing film located in a fiber optic sensor probe 14, the thin sensing film, discussed later, being responsive to the chemical properties of a particular physical quantity to be measured. Changes in the optical characteristics of the thin sensing film of sensor probe 14 are measured by the photometer 12.

As shown in FIG. 1A, photometer 12 comprises light source means 15 which produce light outputs including light at at least two distinct wavelengths. This light from light source means 15 is carried through a single optical fiber 26 to the sensor probe 14, which houses the thin sensing film. As discussed in greater detail below, the optical characteristics of the thin sensing film are responsive to the chemical properties of the measured quantity at the at least two distinct wavelengths of light. These distinct wavelengths of light to which the optical characteristics of the sensing film respond are selected in such a way that when the responses to the at least two distinct wavelengths of light are combined, a self-calibrated measurement of the measured chemical properties is provided. In other words, the at least two distinct wavelengths of light are within the range of wavelengths to which the thin sensing film responds. Thus, it should now be understood that the optical characteristics of the thin sensing film may be responsive to the measured chemical properties at more than two distinct wavelengths of light. However, for purposes of explanation herein, the thin sensing film will be said to respond at the two distinct wavelengths which are selected for measurement.

Photometer 12 further comprises sample detecting means 30 which are connected to the sensor probe 14 through a collection optical fiber 32. The sample detecting means 30 receive the light transmitted from the thin sensing film of sensor probe 14, and measure the optical characteristics of the thin sensing film, such as the optical absorption of the sensing film, by producing light intensity readings at each of the two wavelengths of light. It should be understood that the term "light intensity readings" is intended to refer broadly to some measure of the level of light passing to and from the thin sensing film, and should not be limited to a narrower definition. Photometer 12 also includes reference detecting means 34 which receive the light from the light source means 15 through an optical fiber 28. The reference detecting means 34 sample or monitor the output intensity of the light source means 15 in order to provide continuous compensation for the sample detecting means 30 with respect to fluctuations in the output intensity of the light source means 15.

A signal processing system 35 is provided which is operable for combining the measurements of the optical characteristics of the thin sensing film (i.e., the light intensity readings) in response to each of the two distinct wavelengths in order to provide self-calibrated outputs which account for changes in the optical properties of the thin sensing film. In other words, certain factors, such as changes in the indicator concentration of the thin sensing film, cause the optical characteristics of the sensing film to change, and these changes affect the responses of the sensing film proportionately at the two distinct wavelengths. Thus, by combining the measurements at the two wavelengths (such as by a ratio), these changes are effectively compensated for or cancelled out so that the combined output is self-calibrated with respect to changes in the optical characteristics of the thin sensing film that would otherwise contribute to instability in the sensor response. The reference detecting means 34 are also coupled to the signal processing system 35 for compensating the output with respect to light intensity variations as described above. Finally, the components of the photometer 12 are enclosed in a light isolation box 36 in order to minimize the effect of stray light.

As briefly mentioned above, various implementations can be configured which are encompassed within the broad aspects of the present invention as described above. For example, in a first specific embodiment of the present invention shown in FIG. 1B, light source means 15 comprise first and second light sources 16 and 18 each providing light outputs at distinct and different wavelengths. In this embodiment, the first and second light sources can, for example, be two LEDS, such as a green LED and a red LED which produce light in a relatively narrow spectrum centered at the respective different wavelengths to which the thin sensing film responds. Light source means 15 further comprise a beam splitter 20 which is connected to the light sources 16 and 18 via optical fibers 22 and 24. The beam splitter 20 receives the two distinct wavelengths of light from light sources 16 and 18 and effectively serves as a single light source, in that beam splitter 20 is operable for transmitting the two distinct wavelengths through single optical fiber 26 on a time-shared basis to the thin sensing film of sensor probe 14. The two distinct wavelengths of light are transmitted from the sensor probe 14 to the sample detecting means 30 after the light has passed to and from the thin sensing film. In this embodiment, a single collection fiber 32 couples the sensor probe 14 to a single sample detector 30 which measures the response of the thin sensing film at the respective wavelengths. Additionally, a reference detector 34 is coupled to the beam splitter 20 via optical fiber 28 in such a way that it receives or samples the same light including the two distinct wavelengths conveyed to the sample detector 30 and provides corrections to the sample detector measurements with respect to variations in the output intensity of the light sources.

Figure 1B:
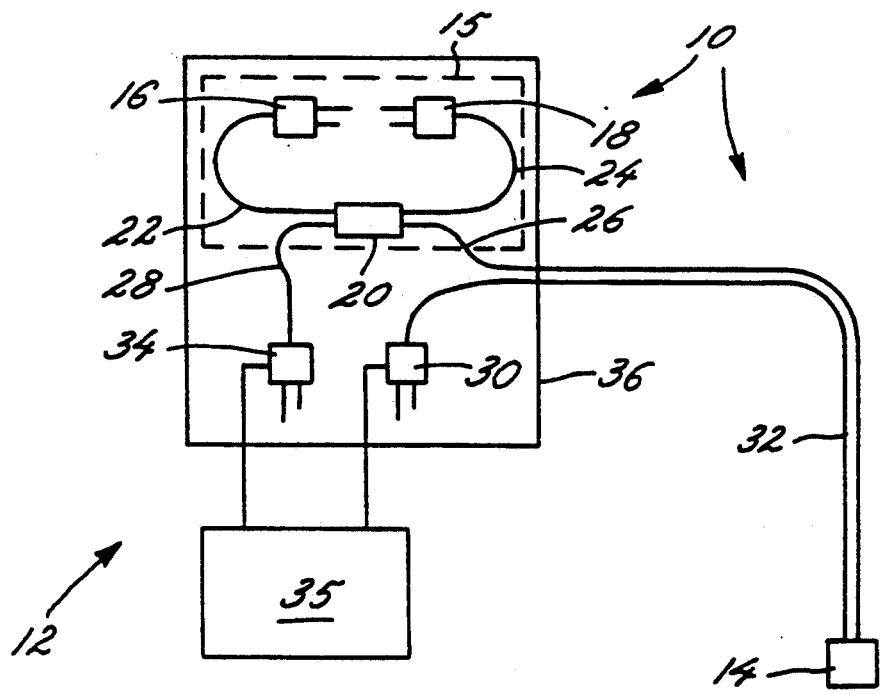
FIG. 1B is a block diagram of a first specific embodiment of the dual wavelength optical sensor shown in FIG. 1A.
Figure 1C:
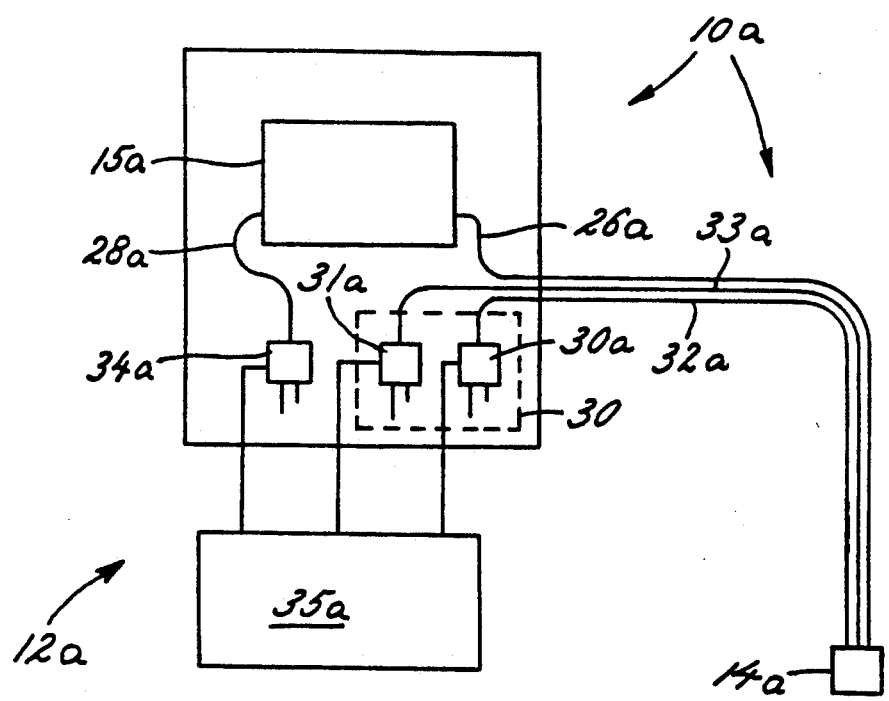
FIG. 1C is a block diagram of a second specific embodiment of the dual wavelength optical sensor shown in FIG. 1A.

In accordance with a second embodiment of the present invention as shown in FIG. 1C, instead of utilizing two narrow spectrum light sources, light source means 15a comprise a single wide spectrum light source which generates multiple wavelength light over a wide spectral range, with the two distinct wavelengths of light being encompassed within this wide spectral range. In at least one respect, this second embodiment is an improvement over the embodiment shown in FIG. 1B, because higher intensity light is provided at the desired wavelengths in this implementation, and electrical components are utilized with greater sensitivity and stability thereby improving overall instrument sensitivity. The wide spectrum light from light source means 15a is carried to sensor probe 14a via a single optical fiber 26a, where it is transmitted to the thin sensing film whose optical characteristics are responsive to the chemical properties of the measured quantity at each of the two distinct wavelengths of light in such a way that when the responses to the two distinct wavelengths of light are combined, a self-calibrated measurement of the chemical properties being measured is provided. As can be seen in FIG. 1C, the sample detecting means in this embodiment comprise two wavelength-selective sample detectors 30a and 31a, which receive the light from sensor probe 14a via two collection fibers 32a and 33a after it has passed to and from the thin sensing film. An alternative to utilizing two collection fibers from the sensor probe 14a to the sample detectors 30a and 31a is to employ a beam splitter which will receive light from the sensor probe 14a via a single collection fiber and transmit twin components of light to each of the respective detectors.

In order to produce light intensity readings at the two distinct wavelengths, the wavelength-selective sample detectors 30a and 31a include filtering means (not shown) selected to respectively pass separate narrow spectrums of light, with each narrow spectrum including light at one of the respective wavelengths. Thus, sample detector 30a produces light intensity readings for a narrow spectrum of light including light at one distinct wavelength, while sample detector 31a produces light intensity readings for a separate narrow spectrum of light including light at the second distinct wavelength. These light intensity readings are then combined by signal processing system 35a to produce output measurements which are self-calibrated with respect to changes in the optical characteristics of the thin sensing film which otherwise contribute to stability problems in the sensor response. Similar to the previous embodiment described above, reference detector 34a samples or monitors the light source which illuminates the thin sensing film. In this particular embodiment, reference 34a detector receives the wide spectrum light generated by light source 15a via optical fiber 28a, and samples or monitors the output intensity of light source 15a to provide compensation to the readings from sample detectors 30a and 31a with respect to spectral variances in the output intensity of the light source.

As stated above, single wavelength optical sensors have been used in the past but tend to produce calibration problems. Additionally, two-wavelength schemes have been developed, but these two-wavelength optical devices do not compensate for variations in the light source output intensities due to time, temperature, and life of the light sources. Of equal if not greater significance is the inability of previous optical sensors to compensate for changes in the optical properties of the thin sensing films which contribute to the instability of the sensor response. For example, changes in the optical properties of the thin sensing films such as changes in the indicator concentration of the films can result from degradation of the films over time, loss of the indicator upon immersion in the measured solutions, and varying levels of indicator concentration at the preparation of the sensing films. In accordance with the present invention, however, the dual wavelength optical sensor of the present invention is capable of compensating and accounting for both changes in the optical properties of the thin sensing film of the sensor probe 14, and for fluctuations in the output intensities of the light source.

An important aspect in achieving these desired results is the ability to use two wavelengths of light, both of which are compatible with (or are within the responsive range of) the thin sensing film, and measuring the optical properties of the thin sensing film at each of the respective wavelengths of light. For example, if the optical properties of the thin sensing film change with time, the response to both wavelengths of light will change in a similar fashion. This allows the response for the two wavelengths to be combined in order to produce a measurement which does not change with the optical properties of the sensing film due to time or other factors. For example, a ratio can be taken of the measurement of the optical absorption of the thin sensing film at each of the two distinct wavelengths of light. By taking this ratio, a measurement can be derived which accounts for changes in the optical properties of the thin sensing film which would otherwise cause or contribute to stability problems in the sensor response. Thus, use of the two distinct wavelengths of light provides long-term stability to the optical sensor of the present invention with respect to changing properties of the thin sensing film.

It should therefore be appreciated by those skilled in the art that the broad confines of the invention encompass an optical sensor including a thin sensing film whose optical characteristics are responsive to the chemical properties of the quantity measured at at least two distinct wavelengths of light in such a way that when the responses to the two distinct wavelengths of light are combined, a self-calibrated measurement of the measured chemical property is provided. The light source for generating these distinct wavelengths of light can be either two narrow spectrum LEDS, as in the embodiment of FIG. 1B, or a wide spectrum light source, like that of the second embodiment described in FIG. 1C, which generates multiple wavelength light including light at the two distinct wavelengths to which the thin sensing film is responsive. Regardless of the particular light source utilized, light intensity readings are produced at each of the respective wavelengths of light by the sample detecting means, with these light intensity readings then combined (as by a ratio) to provide a measurement which is self-calibrated with respect to changes in the optical characteristics of the thin sensing film which otherwise contribute to instability in the sensor response. Additionally, this measurement can also be corrected for inaccuracies due to spectral variances in the light source with the use of the reference detecting means, which samples or monitors the same light that is conveyed to the thin sensing film and measured by the sample detecting means.

Thus, in accordance with the broader aspects of the present invention, a single light source means is provided for illuminating the thin sensing film. In the first embodiment, this is implemented by utilizing a single optical fiber and means for multiplexing the two distinct wavelengths to which the sensing film responds on that single optical fiber. In the second embodiment, this is implemented by utilizing a broad spectrum light source conveyed on the single optical fiber, with the broad spectrum light including the two distinct wavelengths of interest. However, in both embodiments of the present invention described herein, the use of a two-wavelength approach can produce electronic stability problems, relating primarily to the output intensity of the light source means operated in a modulated or switched mode. For example, the light output can change as the light source means are switched on and off for essentially the same input current, and/or the light source temperatures can increase or vary as the light source means are switched on and off.

According to a further aspect of the invention, the dual wavelength optical sensor overcomes these problems by utilizing the reference detector which is coupled in such a way as to monitor or sample the output intensity of the light source means and to provide an indication of light intensity variations. These indications are then used to correct the measurements provided by the sample detecting means. In other words, the reference detector samples the same light that illuminates the thin sensing film and is measured by the sample detecting means, and provides continuous compensation to the measurements of the sample detecting means with respect to fluctuations in the output intensity of the light source means. For example, this continuous compensation can be provided by dividing the optical absorption measurement of the thin sensing film at each distinct wavelength of light by the reference detector measurement at the same distinct wavelength. This quotient provides a measurement which is independent of fluctuations in the output intensities of the light sources. Thus, by compensating for these light source fluctuations, the reference detector allows the effective use of the two-wavelength approach, which in turn allows the optical sensor of the present invention to provide measurements which account for changes in the optical properties of the thin sensing film that would otherwise contribute to instability in the sensor response.

It may prove desirable, as in the second embodiment, to treat the two wavelengths of light conveyed from the thin sensing film to the wavelength-selective sample detecting means separately. For example, since two separate optical collection fibers convey the light from the thin sensing film to the sample detectors, the intensity measurements provided by each sample detector may be separately compensated for any possible differences in the optics. However, that should not detract from the fact that, at least according to this aspect of the invention, it is important to illuminate the thin sensing film as if the light originated from a single light source, independently of whether that light source is a single broad spectrum light source or a pair of multiplexed discrete-wavelength LEDS, with the further subsidiary requirement that the single light source be sampled by the reference detector to compensate for intensity variations of the light source.

By compensating for these problems, the present invention provides an optical sensor such as a pH sensor which has long-term stability and no recalibration requirements. The optical sensor of the present invention can be put in place such as underground or in the body of a biological host for long periods of time and will produce reliable readings calibrated to a known standard for that lengthy interval.

As stated above in connection with the embodiment of FIG. 1B, the two-wavelength light can be transmitted through the single optical fiber 26 to sensor probe 14 on a time-shared basis. This time-sharing (i.e., multiplexing) of a single optical fiber for two distinct wavelengths of light is accomplished with the use of the two light sources 16 and 18, which are electronically modulated or switched at a predetermined frequency in order to transmit the two-wavelength light through the optical fiber 26 on a time-shared basis. By operating in this manner, the dual wavelength photometer of the present invention does not require the use of mechanically moving parts, thus enhancing the mechanical durability of the optical sensor.

In a practical implementation of the first embodiment of the present invention of FIG. 1B, green and red light emitting diodes (LEDS) were utilized as the first and second light sources 16 and 18. The two LEDs 16 and 18 were polished to flatness successively with 32, 15, and 3 $\mu$m abrasive sheets. Polishing provides a smooth and flat surface near the emitting element, thereby enhancing light collection by the optical fibers 22 and 24. The green and red LEDs 16 and 18 have emission maxima (i.e., operating wavelengths) of about 565 and 635 nm, respectively, and bandwidths (at half-height) of about 35 and 40 nm, respectively, so that there is no overlap between the operating wavelengths of the two light sources.

A suitable light source for the light source means of the second embodiment shown in FIG. 1C is a miniature, gas-filled tungsten lamp from Carley Lamps (#T 1½, 631L). The greybody radiator emits over the visible spectrum range, and an end lens on the lamp minimizes energy loss from refraction. Additionally, the lamp should be positioned within an elliptical reflector (such as Carley Lamps, #1580) to focus and collimate energy that would otherwise be lost through spherical radiation.

In one implementation of the first embodiment of the present invention, the fiber optics used for optical fibers 22, 24, 26, 28 and 32 had a 400 $\mu$m core diameter and a 15 $\mu$m thick polymer cladding. Suitable fiber optics of this type are Model No. HCR-M0400T-06, from Ensign-Bickford Optics Co. of Avon, Conn. The optical fibers were also polished successively with 32, 15, 3, and 0.3 $\mu$m abrasive sheets. A 1 cm portion of the protective Tefzel buffer was removed from the fibers at the ends which connect to beam splitter 20 and sensor probe 14, and the fibers were cemented in place with epoxy. The ends of the fibers which connect to the light sources 16 and 18 and to the detectors 30 and 34 were cemented in place with epoxy without removal of the protective buffer.

Figure 2A:
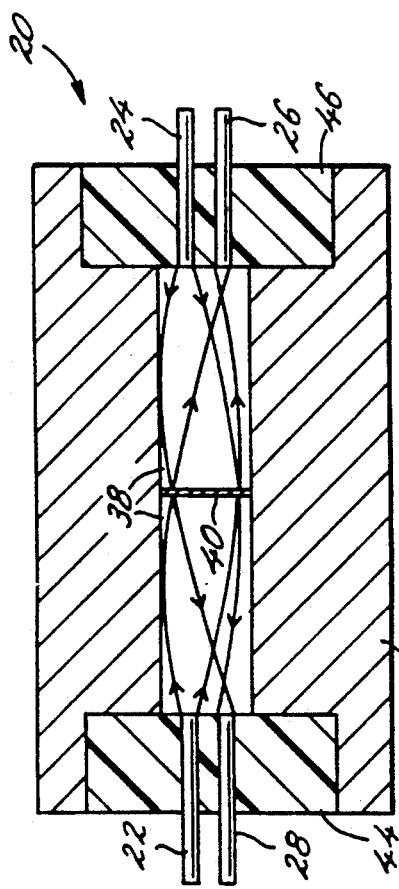
FIG. 2A is a schematic diagram of the beam splitter of the optical sensor shown in FIG. 1B.

Referring again to the drawings, FIG. 2A is a schematic diagram of the beam splitter 20 utilized in the first embodiment as shown in FIG. 1B. In this embodiment, the beam splitter 20 includes a pair of graded-index (GRIN) lenses 38 placed end-to-end, with a beam-splitting, partially reflective metal film 40 deposited on an end of one of the GRIN lenses 38 at the interface of the two lenses 38. A 17 nm chromium film is utilized as metal film 40. The beam splitter 20 is operable for transmitting twin components of light from the LEDs 16 and 18 between the reference detector 34 and the sample detector 30 (via the sensor probe 14). The GRIN lenses 38 are enclosed in a cylindrical brass housing 42, and held end-to-end by Delrin end caps 44 and 46 which properly position the fiber optics for coupling the two-wavelength light between the respective optical fibers. As shown in FIG. 2A, optical fiber 22 from LED 16 and optical fiber 28 are positioned within cap 44, and optical fiber 24 from LED 18 and optical fiber 26 to sensor probe 14 are positioned within cap 46.

In a practical implementation, the beam splitter 20 was constructed from 2.0 mm diameter Selfoc GRIN lenses, Model No. SLW-2.0, from NSG America, Somerset, N.J. The GRIN lenses 38 were 5.11 mm in length and 2.0 mm in diameter. The GRIN lenses 38 were held end-to-end in a cylindrical brass housing with dimensions of 2.5 cm in diameter by 2.3 cm in length.

Figure 2B:
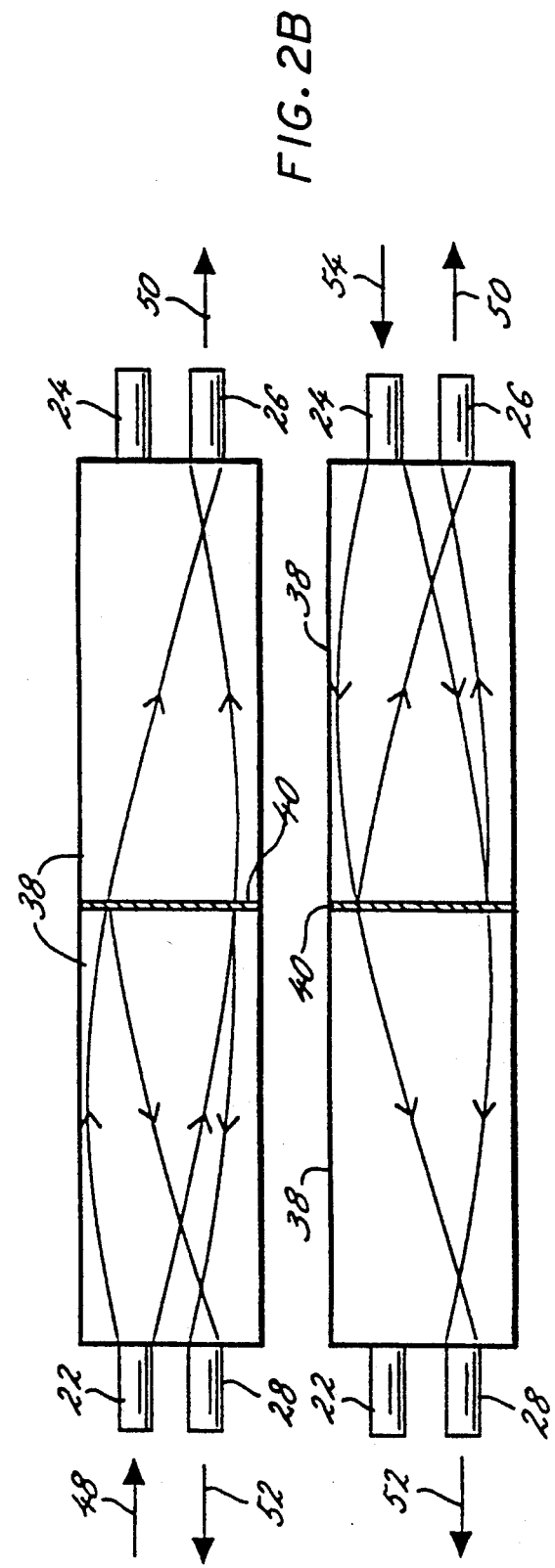
FIG. 2B is an expanded view of the optical lenses of the beam splitter shown in FIG. 2A.

FIG. 2B is an expanded view of GRIN lenses 38 of beam splitter 20 and demonstrates the light propagation path within GRIN lenses 38. The upper and lower diagrams of FIG. 2B demonstrate how beam splitter 20 transmits twin components of the light from LED 16 and LED 18 respectively, to reference detector 34 and sensor probe 14. As shown in the upper view of FIG. 2B, arrow 48 represents light from LED 16 which travels through optical fiber 22 and into GRIN lenses 38. As can be seen, a portion of the light reflects off of metal film 40 and back to fiber 28, while a portion of light travels through the metal film 40 and into optical fiber 26. Thus, arrow 50 represents the light transmitted to sensor probe 14, and arrow 52 represents the light transmitted to reference detector 34. In a similar fashion, the lower view of FIG. 2B demonstrates how beam splitter 20 divides the light from LED 18. Arrow 54 represents the light output of LED 18 which enters GRIN lenses 38 through optical fiber 24. Due to the partially reflective metal film 40, light from LED 18 is transmitted to the reference detector 34, represented as arrow 52, and to the sensor probe 14, represented as arrow 50.

The splitting ratio of the beam splitter 20 was determined by the following method. An optical fiber was connected between one of the outputs of beam splitter 20 and reference detector 34, and the detector response to both wavelengths of light from LEDs 16 and 18 was measured. The fiber was then moved to the other output of beam splitter 20, and the reference detector response to both wavelengths was measured again. The ratio of the detector responses indicated that the relative amounts of transmitted and reflected light were 70% and 30%, respectively. The beam splitter 20 was oriented such that a greater amount of 565 nm light from green LED 16 entered sensor probe 14 than 635 nm light from red LED 18. Because of attenuation at 565 nm by sensor probe 14, however, the relative detector response for the two wavelengths was approximately equal at both detectors 34 and 30.

Optics based on graded-index materials offer advantages of small size and low cost, and are often used for such tasks as coupling light from a source to a fiber optic, collimating light from a fiber, and splitting light between multiple fibers. Unlike conventional lenses, which focus light by refraction at a curved surface of a material with a constant refractive index, GRIN lenses focus light via a refractive index gradient. A GRIN lens is a cylinder with flat ends, with a refractive index as a function of radial distance given by:

$$N(r) = N_o(1 - Ar^2/2)$$

where A is a constant (units of $mm^{-2}$), r is the radial distance (units of mm) from the axis of the lens, and $N_o$ is the refractive index at the axis.

The propagation of rays through a GRIN lens is such that a beam of monochromatic light originating at a point (such as from a fiber optic) at the GRIN lens surface is periodically focused as a function of distance along the GRIN lens axis. Meridional rays propagating through a GRIN lens have a characteristic period of $P = 2\pi/A^{\frac{1}{2}}$. Because light entering one end of a GRIN lens of length nP/2 mm (where n is an integer) is guided to a mirror-image point on the opposite face of the GRIN lens, light can be coupled with high efficiency between two fiber optics placed at the ends of the GRIN lens. Because the refractive index changes as a function of wavelength, however, the period of a lens depends on the wavelength of light.

As stated above, the fiber optic beam splitter 20 as shown in FIG. 2 was constructed with the use of GRIN lenses. Likewise, a GRIN lens (of length P/4 mm) in which the back face is coated with a mirror was used to couple light from two parallel fibers which are placed at the front face of the cylinder along the diameter at equal distances from the axis, as shown in FIG. 3B discussed below.

Figure 3B:
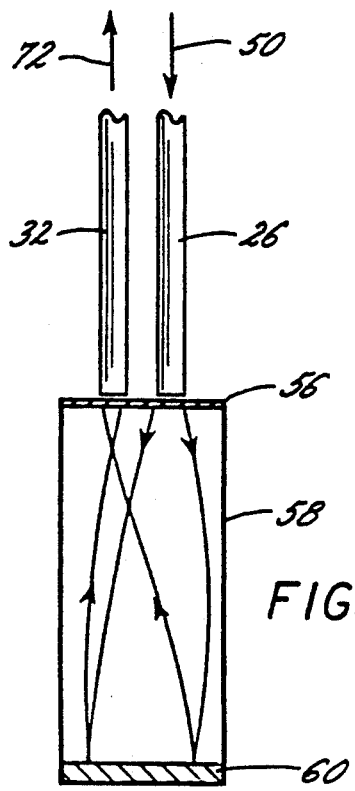
FIG. 3B is an expanded view of the optical lens of the fiber optic sensor probe of FIG. 3A.
Figure 3A:
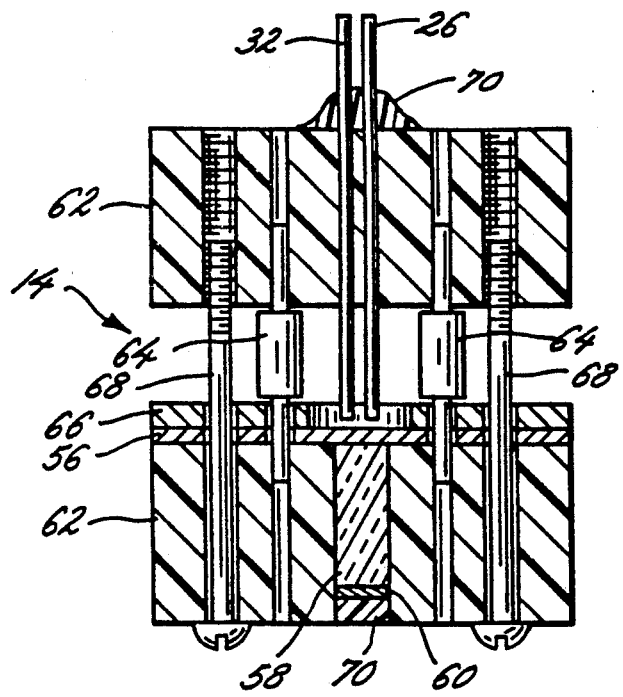
FIG. 3A is a schematic diagram of the fiber optic sensor probe shown in FIGS. 1A and 1B.

FIG. 3A is a diagram of the sensor probe shown in FIGS. 1A and 1B. The sensor probe 14 includes a thin sensing film 56 which is responsive to the chemical properties to be measured, and also responsive to each of the two distinct wavelengths of light in such a way that when the responses to the two distinct wavelengths of light are combined, a self-calibrated measurement of the measured chemical properties is provided. In the preferred embodiments of the present invention, thin sensing film 56 is a pH sensing film. However, other thin sensing films can be utilized in accordance with the present invention for measuring different chemical properties, including physiological parameters such as oxygen, carbon dioxide, sodium, potassium and calcium, as just some examples. Sensor probe 14 also includes a GRIN lens 58 which couples light from optical fiber 26 from beam splitter 20 to collection fiber 32 connected to sample detector 30. The back surface of lens 58 is coated with a reflective film 60 in order to provide the coupling of light efficiently from fiber 26 to collection fiber 32. Although not specifically shown in FIG. 3A, in the second embodiment, two collection fibers 32a and 33a are utilized, with a GRIN lens coupling light from the input fiber 26a to the two collection fibers. In order to maximize light coupling the optical fibers 26a, 32a and 33a are spaced at an equal distance radially around the GRIN lens. In both embodiments, the sensor probe 14 assembly include two Delrin plates 62, which are aligned with stainless steel guide pins 64. The guide pins 64 also provide a means to control the separation between the plates 62, providing a clear path for solution contact. The thin sensing film 56 is mounted on one of the plates 62 and held between the front surface of GRIN lens 58 and fibers 26 and 32 by a stainless steel plate 66. Additionally, plates 62 are held in place with the use of two screws 68, and epoxy 70 is used to secure the optical fibers to the sensor probe 14, and to protect the reflective film 60 from degradation by solution contact.

FIG. 3B is an expanded view of the GRIN lens 58 of sensor probe 14 shown in FIG. 3A. As can be seen in FIG. 3B, the lens 58 of sensor probe 14 receives the two-wavelength light 50 from beam splitter 20 through single optical fiber 26 (in the first embodiment). This light is transmitted to and from the thin sensing film 56 which is responsive to the characteristic to be measured, such as pH. As stated above, the use of GRIN lens 58 allows efficient coupling of the light 50 from fiber 26 to collection fiber 32. As explained in greater detail below, the two-wavelength light transmitted through the collection fiber 32, represented as arrow 72, is received by sample detector 30. The sample detector 30 is operable for measuring the optical absorption of the thin sensing film 56 in response to each of the two distinct wavelengths. In the second embodiment of the invention in which a wide spectrum light source is utilized, two collection fibers 32a and 33a (not shown) respectively transmit the light to wavelength-selective sample detectors 30a and 31a.

In the preferred embodiments of the present invention, the thin sensing film 56 comprises a Congo Red pH sensor. Thus, in the preferred embodiments, sensor probe 14 is a Congo Red sensor probe, and optical sensor 10 is a Congo Red optical sensor. A Congo Red sensing film is a "two-color" indicator, and is operable for measuring PH levels across a large dynamic range (>4 PH units) which results from the polyprotic acid-base reactivity of Congo Red and the high optical absorptivity of its various ionic forms. Depending on the acidic level of the solution to be measured, the Congo Red sensor exhibits effectively two optical states in response to incident light (i.e., visible light). For example, when the Congo Red sensor is subjected to a normal base solution, the sensor appears red in color in response to incident light. When the Congo Red sensor is subjected to a highly acidic solution, the sensor exhibits a blue color in response to incident light. However, regardless of the optical state of the sensor, in the first embodiment of the invention, the two distinct wavelengths of light from the LEDs are selected so that both wavelengths are compatible with each optical state. Similarly, in the second embodiment, a wide spectrum light source is chosen such that the multiple wavelength light generated includes the two wavelengths of light to which the optical states of the Congo Red sensor are responsive. In other words, the Congo Red thin sensing film is responsive to both of the two distinct wavelengths of light for each optical state of the sensing film. As explained in greater detail below, this allows the optical sensor of the present invention to provide internally calibrated measurements across a large dynamic range of PH units which are independent of the indicator concentration of the thin sensing film.

The thin sensing film 56 was fabricated by spin-coating a 15% (w/v) solution of cellulose acetate and cyclohexanone at 2,000 rpm onto glass microscope slides. The concentration of the cellulose acetate was high enough to provide films having substantial mechanical strength. After drying for 24 hours in air, the films were hydrolyzed in 0.1M KOH for 24 hours. Congo Red was immobilized according to a standard dye-bath recipe, and is sensitive in the pH range from 4.5 to 0.0. Thin sensing film 56 was mounted in sensor probe 14, and held in place by stainless steel plate 66 having a 1 mm thickness with a 5 mm hole to expose the ph-sensitive thin sensing film 56 to the solution to be measured.

Figure 4A:
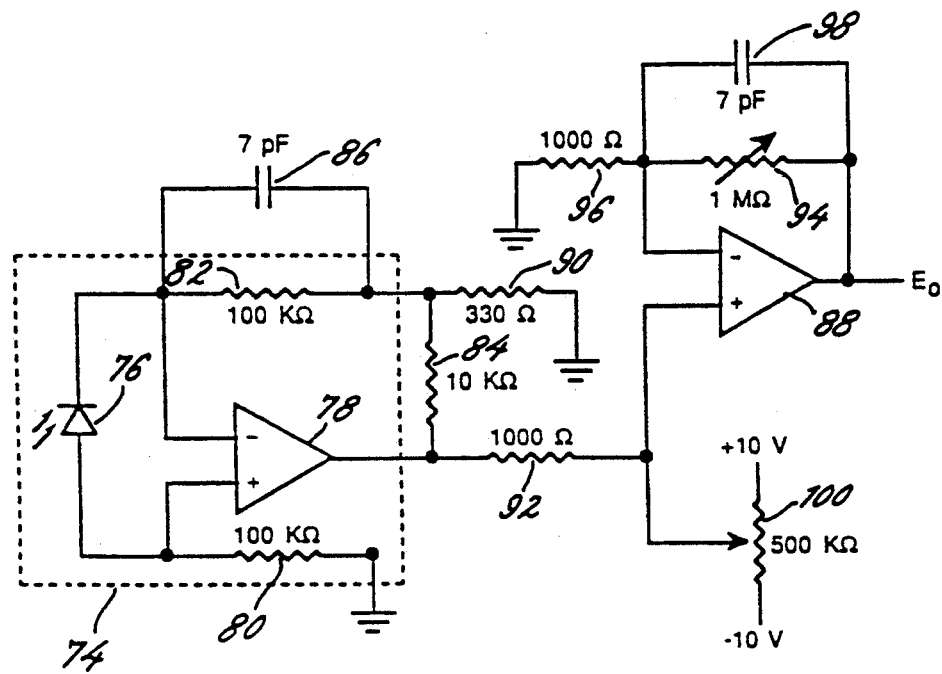
FIG. 4A is a schematic diagram of the electronic circuitry for the sample detector and the reference detector shown in the first embodiment of FIG. 1B.

FIG. 4A is a schematic diagram of the electronic circuitry of sample detector 30 and reference detector 34 in the first embodiment of the present invention as depicted in FIG. 1B. As stated previously, sample detector 30 provides a measurement of the optical absorption of thin sensing film 56 at each of the two distinct wavelengths, and reference detector 34 measures the output intensities of LEDs 16 and 18 in order to provide continuous compensation to sample detector 30 with respect to fluctuations in the output intensities of LEDs 16 and 18. In both detectors 30 and 34, a photodetector 74 is utilized, which contains a 5.0-mm$^2$ silicon photodiode 76 connected to an internally packaged low-noise preamplifier 78. A suitable photodetector is Model No. S529-01-5 from Devar, Inc., of Bridgeport, Conn. The preamplifier 78 includes a resistor 80 connected between its non-inverting input and ground. Additionally, resistors 82 and 84 and a capacitor 86 are connected between the inverting input of preamplifier 78 and its output, and a resistor 90 is connected to ground. The output voltage from photodetector 74 is amplified by an operational amplifier 88 having adjustable gain and zero offset. A resistor 92 is connected between the output of preamplifier 78 and the non-inverting input of amplifier 88. Additionally, a variable resistor 94, a resistor 96, and a capacitor 98 are connected between the inverting input of amplifier 88 and its output. Finally, an A/D converter (not shown) is configured for $+/-10V$ through a potentiometer 100, which results in a 0.3 mV resolution. The noise level of the signal ($+/-7.5$ my) was 25 times the resolution of the A/D converter.

Figure 4B:
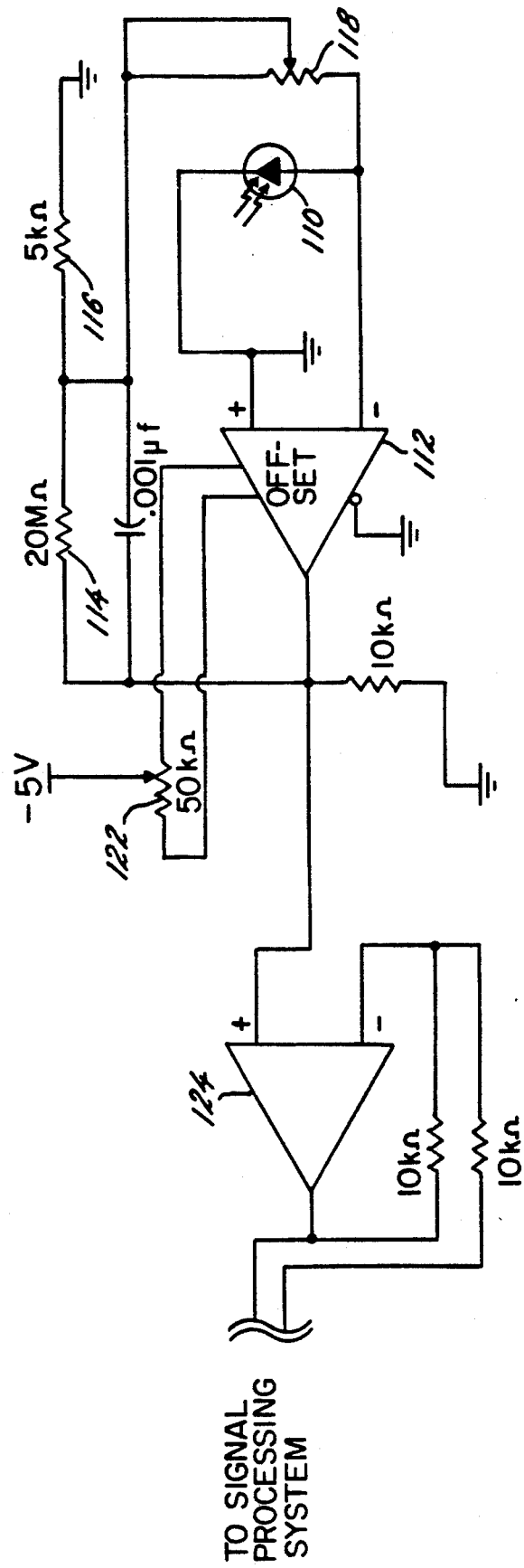
FIG. 4B is a schematic diagram of the electronic circuitry for the sample detectors and the reference detectors shown in the second embodiment of FIG. 1C.

In the second embodiment of the present invention, electrical components with greater sensitivity and stability are utilized to improve overall instrument sensitivity. FIG. 4B is a schematic diagram of the electronic circuitry of the wavelength-selective sample detectors 30a and 31a and the reference detector 34a as shown in FIG. 1C. In this embodiment, because a wide spectrum light source is utilized, both of the sample detectors 30a and 31a receive the multiple wavelength light after it has passed to and from the thin sensing film 56. In order to produce light intensity readings at the two distinct wavelengths to which the thin sensing film is responsive, interference filters (not shown) are provided in the detector housings which filter and focus narrow spectrums of light upon the detectors. Thus, the interference filter associated with detector 30a filters a first narrow spectrum of light including light at one of the respective wavelengths, and the other interference filter associated with detector 31a filters a second narrow spectrum of light including light at the other respective wavelength. For example, when a Congo Red sensor is utilized, the interference filters are selected to pass narrow spectrums of light on the order of 10 nm, with the 565 nm wavelength included in one narrow spectrum, and the 635 nm light included within the second narrow spectrum.

Referring specifically to FIG. 4B, a silicon photodiode 110 receives the transmitted light, and produces an output signal proportional to the light intensity at the selected wavelength, which is coupled to an internally packaged preamplifier 112. A suitable photodiode is Model No. VTB 9414 of EG&G VACTEC, with active areas of 1.6 mm$^2$. The photodiode 110 is connected in the photovoltaic mode to preamplifier 112, which is a transimpedance operational amplifier produced by Analog Devices, Model No. AD549. These operational amplifiers have a co on-mode impedance of $10^{15}$ ohms with an extremity low bias current of 250 fA maximum, and perform well as sensitive photodiode preamplifiers because of their low input current and offset voltage characteristics. Gain is achieved with the use of feedback resistance, via resistors 114, 116 and 118 and capacitor 120. Preamplifier 112 also includes zero offset via adjustable resistor 122. The output signal from preamplifier 112 is amplified by an operational amplifier 124, whose output is then coupled to the signal processing system 35 as explained in further detail below. The output signal of amplifier 124 is connected to the inverting input of amplifier 124 via resistors 126 and 128.

In order to monitor and manipulate the measurements of the sample detectors and reference detectors, a signal processing system 35 is utilized as shown in FIGS 1A, 1B and 1C. In a practical implementation of the present invention, signal processing system 35 included an 80386-based microcomputer with RTI-815 and RTI-850 data acquisition boards, produced by Analog Devices of Norwood, Mass. The data acquisition boards were controlled with "Labtech Notebook" software from Laboratory Technology Corp., of Wilmington, Mass. Thus, while the remaining Figures depict data associated with the first embodiment of the present invention, it should be appreciated that the optical sensor of the second embodiment responds and operates like that of the first embodiment, and that sensor measurements and data collection would be similar to that shown below. In fact, as mentioned above, overall instrument sensitivity is improved with the optical sensor of the second embodiment since the wide spectrum tungsten light source produces higher intensity light at the desired wavelengths, and electrical components are utilized with greater sensitivity and stability.

Figure 5A:
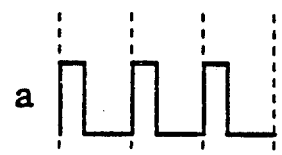
FIGS. 5A–5C are waveforms representing the light source output and detector responses for the first embodiment shown in FIG. 1B.
Figure 5B:
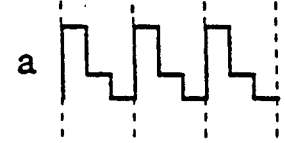
Figure 5C:

Turning now to the first embodiment of the present invention, FIG. 5A shows the output waveforms of red LED 18 (waveform a) and green LED 16 (waveform b) in response to an applied voltage. The LEDs 16 and 18 were electronically modulated at 24 Hz through 8-bit analog output channels on the RTI-815 acquisition board. FIGS. 5B and 5C are waveforms of the responses of sample detector 30 and reference detector 34, respectively, resulting from illumination of LEDs 16 and 18. In FIGS. 5A-5C, the value of t for the time base is 1/24 seconds. Additionally, all Y-axes are in arbitrary units with the detector voltage used to indicate the lower sensitivity of detectors 30 and 34 to light at 565 nm from the green LED 16. The sample and reference detector voltages were measured with 16-bit analog input channels on the RTI-850 and represented 24 Hz square-wave functions of detector voltage comprising three stages: (1) illumination by red LED 18 as shown in waveforms b of FIGS. 5B-5C, (2) illumination by green LED 16 as shown in waveforms c of FIGS. 5B-5C, and (3) illumination by only background, with both LEDs off as shown in waveforms d of FIGS. 5B-5C. Each LED was switched on by applying a 7.8V potential, resulting in a 20 mA current through each LED.

The absorbances of the optical sensor of the present invention at 565 nm and 635 nm were monitored as a function of time as sensor probe 14 was inserted into solutions of varying pH. The solutions were stirred with a magnetic stirring bar, and the sensor probe 14 was rinsed with deionized water between immersions to minimize solution carry-over. The response of optical sensor 10 was allowed to reach a constant value in each of the varying solutions. The absorbance vs. time trace was smoothed with a nine-point Savitsky-Golay smoothing algorithm. The time constant of the optical sensor 10 response was determined as the time required for 63% of the maximum response. Additionally, the pH of the solutions was controlled by varying the amounts of HCl or KOH, and sufficient KCl was added to adjust the ionic strength to 0.1. All solutions were prepared with deionized water.

Figure 6A:
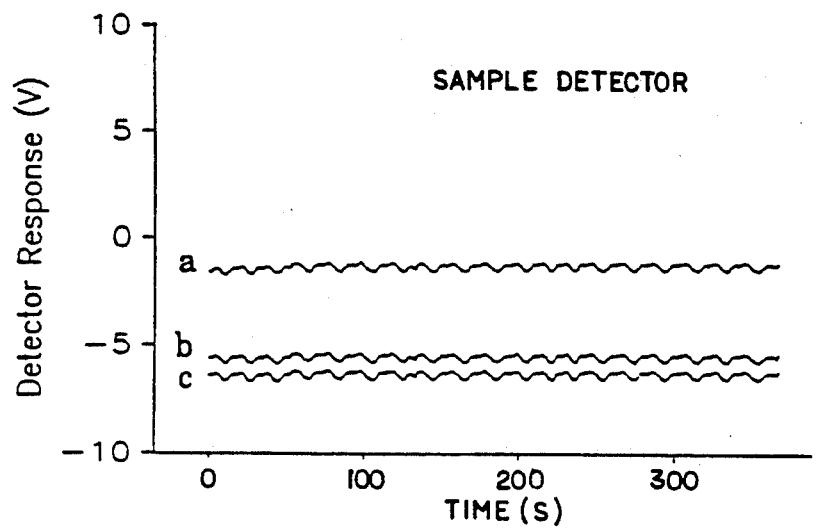
FIGS. 6A–6B are waveforms showing the time-based responses of the sample detector and the reference detector, respectively, to illumination of the light sources for the first embodiment of FIG. 1B.
Figure 6B:
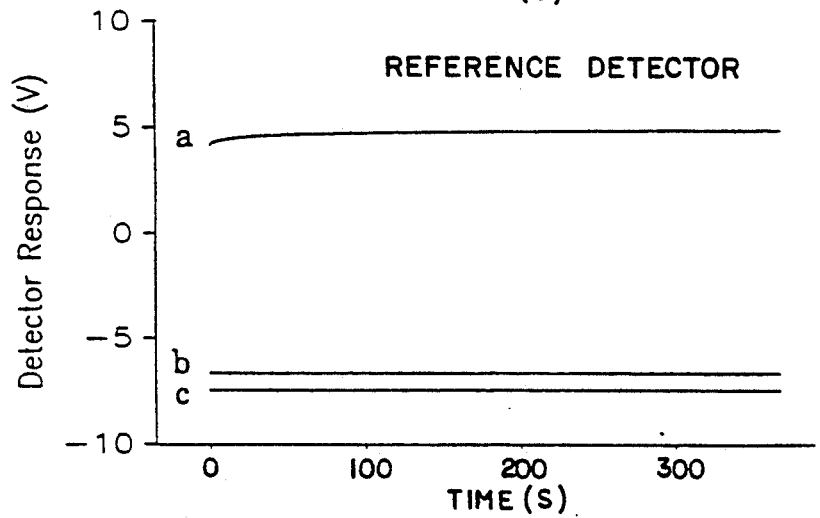

FIGS. 6A and 6B show the amplified detector voltages of the sample and reference detectors 30 and 34 in connection with the first embodiment, respectively, as a function of time for illumination by: (a) red LED 18, (b) green LED 16, and (c) background (LEDs off). The traces in FIGS. 6A-6B represent a signal-average over intervals of one second (8 data-points per second) of the detector responses, which at this time base appear continuous. The periodic variations in the response of sample detector 30 in FIG. 6A are from stray light (fluorescent room lights) which enters through sensor probe 14. The subtraction of the detector background-voltage, however, compensates for variations in the background intensity. The slow increase observed in the early portion of trace (a) in FIG. 6B is due to thermal variations in the output of the red and green LEDs 18 and 16. At the initial stages of data acquisition, the current through each LED causes its temperature to increase until reaching a steady-state value. However, in accordance with the present invention, this variation is effectively compensated by measurement of the LED outputs with reference detector 34.

Figure 6C:
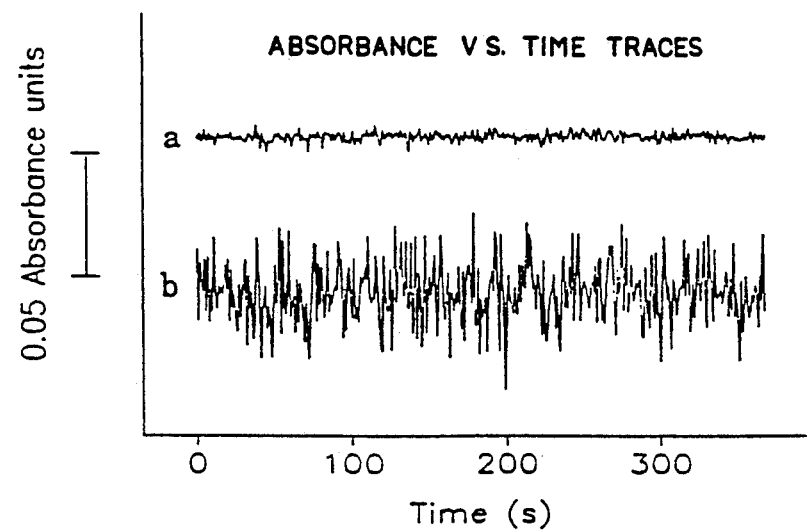
FIG. 6C are waveforms showing the absorbance vs. time traces at the two distinct wavelengths of light using the data from FIGS. 6A–6B.

Because the voltages of the detector outputs are a linear function of the intensity of incident light, the absorbance of the thin sensing film 56 of sensor probe 14 at each of the two wavelengths is given by $$A = -log[f_s(V_{s,i} - V_{s,b})]/[f_r(V_{r,i} - V_{r,b})]\qquad(1)$$

where V represents detector voltage, and f represents a proportionality constant arising from a number of factors (e.g., gain of sample and reference detectors, splitting ratio of beam splitter 20, and light attenuation by the sensor probe 14 and fiber-optics). The subscripts s and r refer to sample and reference detectors, respectively, and the subscripts i and b represent the detector-illuminated voltage and background voltage, respectively. Equation (1) can be rearranged to give $$A = -log[(V_{s,i} - V_{s,b})/(V_{r,i} - V_{r,b})] + C\qquad(2)$$

where c represents $-log(f_s/f_r)$. The sensor probe 14 was assembled without a sensing film 56, and the values of C were determined for absorbance determinations at both 635 and 565 nm. Subtraction of $V_b$ corrected for detector dark-current, voltage offset of the operational amplifier, and stray light. The absorbance-vs.-time traces at 635 and 565 nm are shown in FIG. 6C. The absorbances were calculated by Equation (2) using the data from FIGS. 6A and 6B. The root-mean-square noise levels were +/−0.002 and +/−0.013 for the absorbances at 635 and 565 nm, respectively. The difference in noise level between these two wavelengths is attributed to two factors: (1565-nm light couples through sensor probe 14 with only about 53% of the efficiency as 630-nm light, and (2) the detector response for 565-nm light is about 30% of the response for 635-nm light. Improvements in the noise level of the absorbance measurement at 565 nm can be accomplished by utilizing detectors with a greater sensitivity to 565-nm light, and higher-intensity light sources. In that respect, improvements have been achieved with the optical sensor according to the second embodiment of the present invention, since the wide spectrum tungsten light source generates 565-nm light at approximately the same intensity level as 635-nm light, and since electrical components with greater sensitivity and stability are utilized as explained above in connection with FIG. 4B. Additionally, an increase in the data collection rate will reduce the contribution of 1/f noise, which will result in further noise reduction.

In the second embodiment, the wide spectrum light source 15a is also switched on and off, but not for the purposes of multiplexing the light onto the single optical fiber, as is done in the first embodiment when utilizing two LEDS. Rather, the light source is switched off periodically to take readings which quantify the electronic noise in the system and any stray light present. Further, when the light source is switched on, the reference detector 34a and the sample detectors 30a and 31a receive light at the same time, so that the reference detector can sample or monitor light intensity variations. These corrective readings can then be combined with the readings from the sample detectors taken when the light source is turned on in order to provide overall measurements which are compensated for light source fluctuations, electronic noise, and the like. After the electronic noise is quantified when the light source is off, the light source is turned on and allowed to reach a steady intensity. Then, a plurality of measurements or readings are taken during each "on" interval, and either each measurement or an average of the measurements for the specific interval can be utilized in producing an overall output reading. Thus, the optical sensor of the present invention not only provides measurements which are internally calibrated with respect to variations in the optical characteristics of the thin sensing film, but which are also calibrated with respect to light source fluctuations and electronic noise in the system.

Figure 7A:
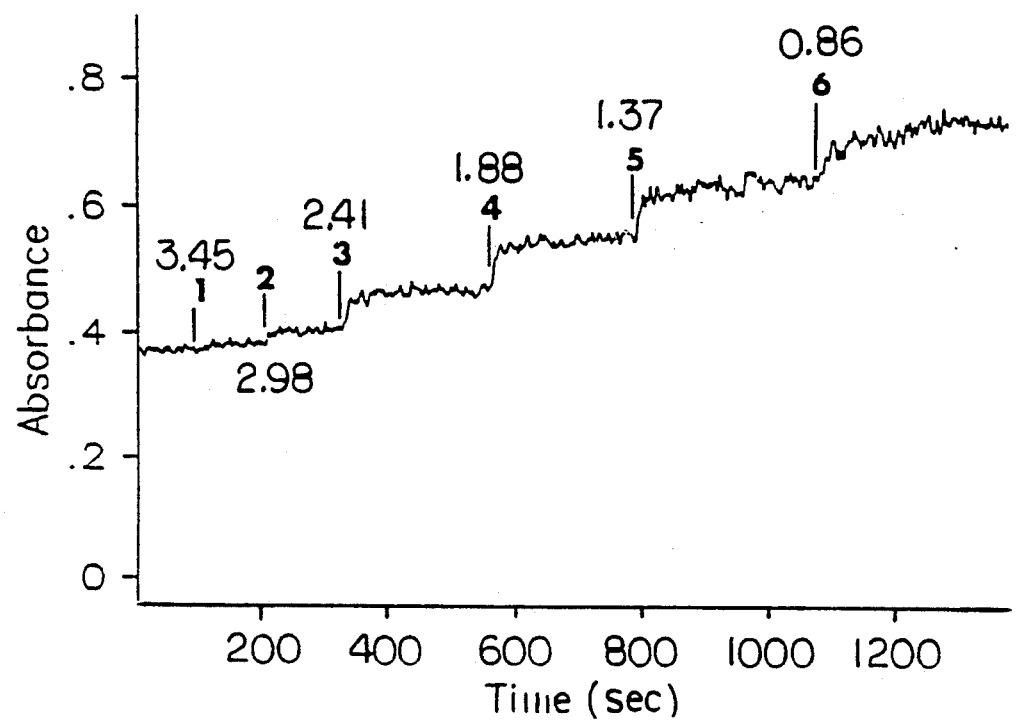
FIGS. 7A–7B are waveforms of the absorbance time response of the thin film sensor to changes in pH at the first and second wavelengths of light, respectively for the first embodiment shown in FIG. 1B.
Figure 7B:
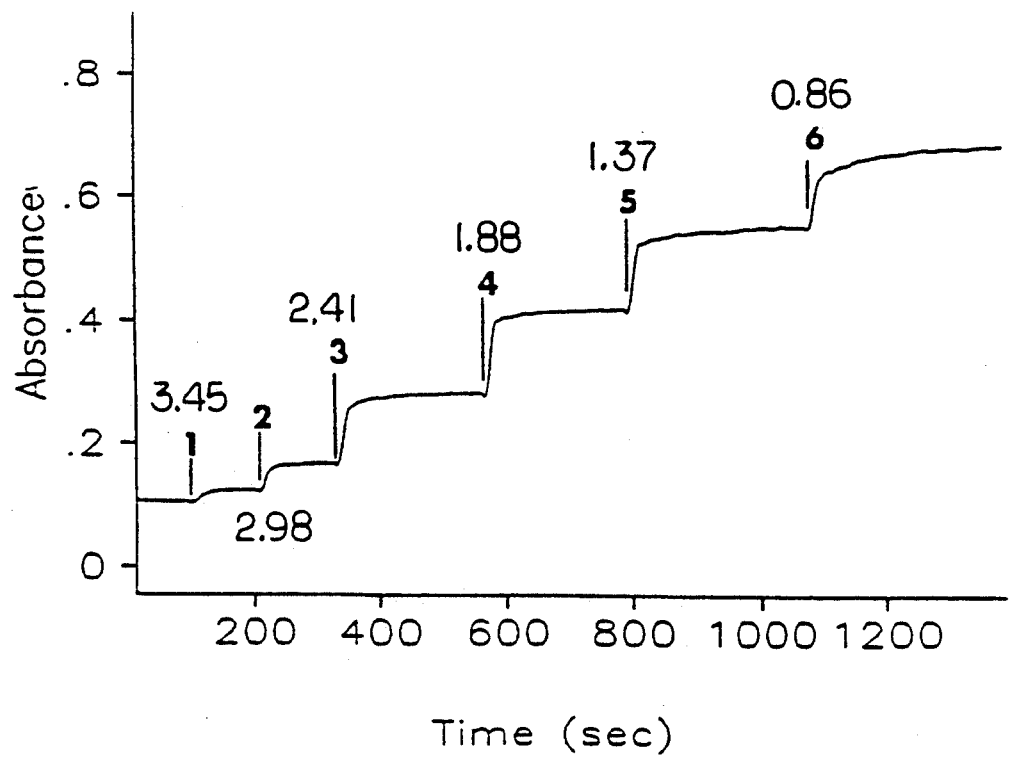

Referring again to the first embodiment, the performance of the dual-wavelength photometer of the present invention was tested with a Congo Red thin-film sensor probe 14, which responds across a range from pH 0 to 4. The LEDs 16 and 18 were electronically modulated at 24 Hz. The absorbances at 565 and 635 nm were calculated from the detector voltages by Equation (2), and were displayed in real-time on a computer screen. FIGS. 7A-7B show the response of the absorbance of the Congo Red sensor probe 14 at 565 nm (FIG. 7A) and 635 nm (FIG. 7B) as the sensor probe 14 was inserted into solutions of differing pH. The hash marks adjacent the waveforms in FIGS. 7A-7B indicate the times at which the pH level of the measured solutions was changed, and the numerical values above or below the hash marks indicate the corresponding pH levels. As the pH of the solutions decreased, the absorbance at both 565 and 635 nm increased until they reached a limiting value. The small negative-going "spikes" at each sample change are an artifact resulting from the Savitsky-Golay smoothing algorithm. Although sensor probe 14 was rinsed with deionized water between immersions, no sensor response was observed when the sample probe was rinsed with deionized water, due to its low ionic strength. The time constant for the response of the Congo Red sensor probe 14 upon immersion in the pH standards was 10 seconds, which represents the time required for solution mixing as well as the sensor response. A preliminary stability test of the response of photometer 12 was determined over a four-hour period, during which no detectable change in absorbance was observed.

Figure 8:
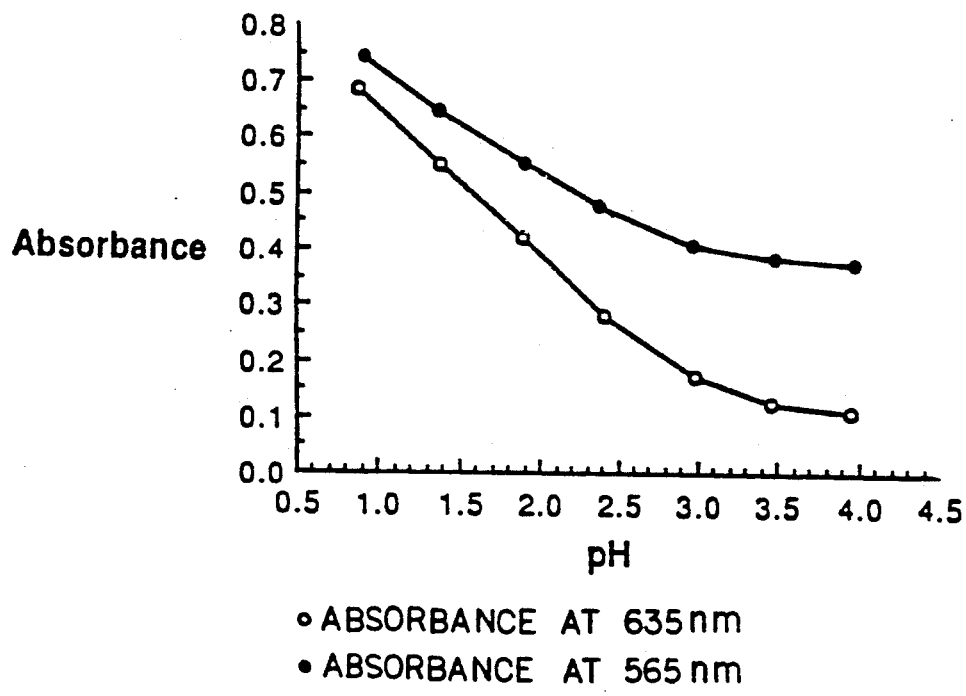
FIG. 8 is a graph of the absorbance as a function of pH for the thin film optical sensor of the first embodiment of the present invention shown in FIG. 1B.

FIG. 8 shows the absorbance at 565 nm and 635 nm as a function of pH for the Congo Red sensor probe 14. The peak-to-peak noise level for the absorbance at 635 nm was ±0.001. This level of noise allows the singe-wavelength detection of changes in pH as small as 0.003 pH units. The peak-to-peak noise level for the absorbance at 565 nm was ±0.010. As noted before, the higher noise level for 565-nm light is due to the lower sensitivity of the detectors and the lower coupling efficiency of the sensor probe 14 for this wavelength. However, as explained above, the wide spectrum light source of the second embodiment produces higher intensity light at 565 nm so that the noise level at this wavelength is reduced.

Figure 9:
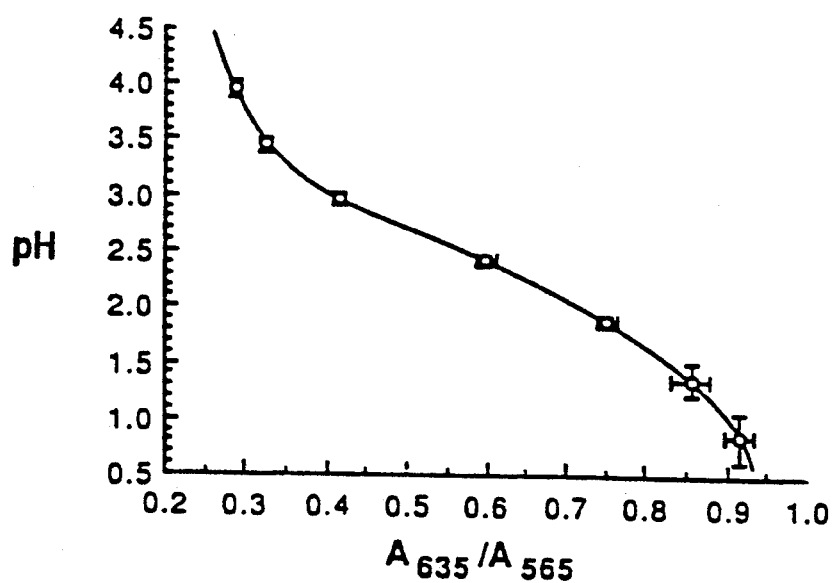
FIG. 9 is a calibration curve for the thin film optical sensor of the first embodiment of the present invention shown in FIG. 1B.

One advantage of a "two-color" indicator (such as Congo Red) is that a calibration curve that is independent of indicator concentration can be constructed. As stated previously, changes in the indicator concentration of the thin sensing films can result from degradation of the films over time, loss of indicator upon immersion in the measured solutions, and varying levels of indicator concentration at the preparation of the thin sensing films. However, by utilizing the dual wavelength approach, the optical sensor of the present invention can realize calibration that is independent of the indicator concentration. For example, FIG. 9 shows a calibration curve for the Congo Red optical sensor 10 of the present invention, which was obtained by plotting the pH as a function of the ratio of the absorbance at 635 nm to the absorbance at 565 nm ($A_{635}/A_{565}$) Again, although not shown, measurements taken with the optical sensor according to the second embodiment of the present invention would produce a calibration carve like that shown in FIG. 9. Thus, the dual wavelength approach of the present invention provides an absorbance ratio that results in a calibration which is independent of indicator concentration. Therefore, in accordance with the present invention, the dual wavelength optical sensor 10 can compensate and account for changes in the optical properties of the thin sensing films due to time and other factors, and thus achieve long-term stability with no recalibration requirements.

The two-wavelength calibration approach was determined to be reproducible for sensor films containing differing amounts of indicator to within +/−0.05 pH units. The data were then fitted with a fifth-order polynomial equation to give $$pH = 28.75 - 215.6r + 720.3r^2 - 1195r^3 + 972.5r^4 - 31 - 1.9r^5 \quad (3)$$

for the Congo Red sensor, where r is the absorbance ratio ($A_{635}/A_{565}$). The horizontal error bars in FIG. 9 represent the uncertainty in the measurement of the absorbance ratio. The vertical error bars in FIG. 9 represent the uncertainty in the calculated pH corresponding to the uncertainty in r, via the derivative of Equation (3). The uncertainty in the pH calculated by Equation (3) varies from a low of +/−0.03 in the middle of the calibration curve to +/−0.08 and +/−0.22 at the high-pH and low-ph ends, respectively. The greater uncertainty in pH at the ends of the calibration curves arises from the large change in pH corresponding to a small change in absorbance ratio. Additionally, although the bandwidth (in excess of 30 nm) of LEDs 16 and 18 causes nonlinearity of Beer-Lambert plots, this nonlinearity does not affect the accuracy of calibration plots like that shown in FIG. 9.

Particular applications of the optical sensor of the present invention include the construction of "remote sensing modules" (RSM), which provide continuous environmental sensing at multiple remote locations, such as underground water systems. Additionally, the optical sensor of the present invention can be used in sensors for biomedical applications, such as the measurement of physiological pH, sodium, potassium, or calcium. The RSMS, which contain on-board microprocessors and FM-radio transceivers, can be placed at multiple locations along a watershed, and interrogated by a central data station located in a vehicle or communicating via microwave repeater stations.

As is evident from the foregoing description, the present invention provides a solid-state optical photometer and fiber optic sensor probe that operates in a two-wavelength mode for producing long-term absorbance measurements with no recalibration requirements. The optical sensor of the present invention is capable of compensating for fluctuations in output intensities of the light source in order to provide continuous calibration to the optical sensor with respect to the light source outputs. Additionally, the optical sensor of the present invention provides long-term stability and eliminates recalibration problems by also compensating and accounting for changes in the optical properties of the thin sensing films due to time, degradation, losses, etc., which contribute to the instability of the sensor response.

We claim:

1. A dual wavelength optical sensor for measuring chemical properties of a particular quantity comprising:
   a sensor probe including a thin sensing film whose optical characteristics are responsive to the chemical properties of the quantity at at least two distinct wavelengths of light in such a way that when the responses to the at least two distinct wavelengths are combined, a self-calibrated measurement of the measured chemical properties is provided;
   light source means for generating the at least two distinct wavelengths of light, and a single optical fiber for carrying the light from the light source means to the sensor probe;
   sample detecting means receiving the light from the sensor probe after it has passed to and from the thin sensing film and producing light intensity readings for the at least two distinct wavelengths of light; and
   output means for combining the light intensity readings from the sample detecting means to produce the self-calibrated measurement which accounts for changes in the optical characteristics of the thin sensing film that otherwise contribute to instability in the sensor response.

2. The optical sensor as set forth in claim 1 wherein the light source means comprise first and second light emitting diodes, the first light emitting diode producing light at one of the at least two distinct wavelengths to which the thin sensing film is responsive, and the second light emitting diode producing light at another of the at least two distinct wavelengths to which the thin sensing film is responsive.

3. The optical sensor as set forth in claim 2 further comprising means for multiplexing the two distinct wavelengths of light from the respective light emitting diodes onto the single optical fiber.

4. The optical sensor as set forth in claim 1 wherein the light source means generates multiple wavelength light over a wide spectral range, the at least two distinct wavelengths of light being encompassed within said wide spectral range.

5. The optical sensor as set forth in claim 4 wherein the sample detecting means include filtering means for rendering the sample detecting means selectively responsive to the at least two distinct wavelengths of light.

6. The optical sensor as set forth in claim 1 further comprising reference detecting means coupled to the light source means in such a way as to monitor the output intensity of the light source means to provide compensation to the readings produced by the sample detecting means with respect to spectral variances in the output intensity of the light source means.

7. The optical sensor as set forth in claim 1 wherein the output means comprise a signal processing system operable for taking a ratio of the light intensity readings produced by the sample detecting means to provide the self-calibrated measurement which accounts for changes in the optical characteristics of the thin sensing film that otherwise contribute to instability in the sensor response.

8. The optical sensor as set forth in claim 1 wherein the thin sensing film is based on the immobilization of Congo Red in a porous polymer film.

9. A dual wavelength optical sensor for measuring chemical properties based on the optical characteristics of thin sensing films which are responsive to at least two distinct wavelengths of light, the optical sensor comprising:
   light source means for producing light outputs at the at least two distinct wavelengths;
   a single optical fiber receiving the at least two distinct wavelengths of light from the light source means and carrying the light to a sensor probe;
   the sensor probe transmitting the at least two distinct wavelengths of light to and from a thin sensing film associated with the sensor probe, the thin sensing including optical characteristics which produce responses at the at least two distinct wavelengths which, when combined, provide a self-calibrated measurement of the chemical properties being measured;
   sample detecting means receiving the at least two distinct wavelengths of light transmitted from the thin sensing film and measuring the optical characteristics of the thin sensing film in response to the at least two distinct wavelengths of light; and
   means combining the measurements of the optical characteristics of the thin sensing film from the sample detecting means for providing the self-calibrated measurements which account for changes in the optical characteristics of the thin sensing film that otherwise contribute to instability in the sensor response.

10. The optical sensor as set forth in claim 9 further comprising reference detecting means coupled to the light source means in such a way as to monitor the output intensity of the light source means to provide compensation to the measurements produced by the sample detecting means with respect to spectral variances in the output intensity of the light source means.

11. The optical sensor as set forth in claim 10 wherein the light source means comprise first and second light emitting diodes, the first light emitting diode producing light at one of the at least two distinct wavelengths to which the thin sensing film is responsive, and the second light emitting diode producing light at another of the at least two distinct wavelengths to which the thin sensing film is responsive.

12. The optical sensor as set forth in claim 11 further comprising means for multiplexing the two distinct wavelengths of light from the respective light emitting diodes onto the single optical fiber.

13. The optical sensor as set forth in claim 10 wherein the light source means generates multiple wavelength light over a wide spectral range, the at least two distinct wavelengths of light being encompassed within said wide spectral range.

14. The optical sensor as set forth in claim 13 wherein the sample detecting means include filtering means for rendering the sample detecting means selectively responsive to the at least two distinct wavelengths of light.

15. The optical sensor as set forth in claim 9 wherein the combining means comprise a signal processing system operable for taking a ratio of the light intensity readings produced by the sample detecting means to provide the self-calibrated measurement which accounts for changes in the optical characteristics of the thin sensing film that otherwise contribute to instability in the sensor response.

16. The optical sensor as set forth in claim 9 wherein the thin sensing film is based on the immobilization of Congo Red in a porous polymer film.

17. A method of measuring chemical properties of a particular quantity based on the optical characteristics of thin sensing films which are responsive to at least two distinct wavelengths of light, the method comprising:
 producing light at the at least two distinct wavelengths;
 conveying the light through a single optical fiber to a thin sensing film;
 subjecting the thin sensing film to the chemical properties to be measured to produce responsive optical characteristics at the at least two distinct wavelengths which, when combined, provide a self-calibrated measurement of the chemical properties being measured;
 receiving the at least two distinct wavelengths of light from the thin sensing film and measuring the optical characteristics of the thin sensing film in response to the at least two distinct wavelengths of light; and
 combining the measurements of the optical characteristics of the thin sensing film for providing the self-calibrated measurement which accounts for changes in the optical characteristics of the thin sensing film that otherwise contribute to instability in the sensing response.

18. The method of claim 17 wherein the light at the at least two distinct wavelengths is produced by first and second light emitting diodes, the first light emitting diode providing light at one of the at least two distinct wavelengths, and the second light emitting diode providing light at another of the at least two distinct wavelengths.

19. The method of claim 18 further comprising the step of multiplexing the two distinct wavelengths of light from the respective light emitting diodes onto the single optical fiber.

20. The method of claim 17 wherein the light is produced by a single wide spectrum light source generating multiple wavelengths of light, the at least two distinct wavelengths of light included among the multiple wavelengths of light.

21. The method of claim 17 further comprising the step of monitoring the output intensity of the light and compensating the measurements of the optical characteristics of the thin sensing film with respect to spectral variances in the output intensity of the light.

22. The method of claim 17 wherein the step of combining comprises taking a ratio of the measurements of the optical characteristics of the thin sensing film in response to the at least two distinct wavelengths of light to provide the self-calibrated measurement.

23. The method of claim 17 wherein the thin sensing film is based on the immobilization of Congo Red in a porous polymer film.

24. A dual wavelength optical sensor for measuring the optical characteristics of thin sensing films which are responsive to the chemical properties of a particular quantity to be measured, the optical sensor comprising:
 light source means for producing light at two distinct wavelengths;
 a time-shared optical fiber receiving the two distinct wavelengths of light from the light source means and carrying the two distinct wavelengths on a time-shared basis to a sensor probe;
 the sensor probe transmitting the two distinct wavelengths of light to and from a thin sensing film associated with the sensor probe, the optical characteristics of the thin sensing film being responsive to the chemical properties of the quantity at the two distinct wavelengths in such a way that when the responses to the two distinct wavelengths are combined, a self-calibrated measurement of the measured chemical properties is provided;
 sample detecting means receiving the two distinct wavelengths of light transmitted from the thin sensing film and measuring the optical characteristics of the thin sensing film in response to the two distinct wavelengths of light; and
 means combining the measurements of the optical characteristics of the thin sensing film in response to each of the two distinct wavelengths for providing the self-calibrated measurement which accounts for changes in the optical characteristics of the thin sensing film that otherwise contribute to instability in the sensor response.

25. The optical sensor as set forth in claim 24 further comprising reference detecting means sampling the same light transmitted to the thin sensing film from the light source means for providing continuous compensation to the measurements of the sample detecting means with respect to fluctuations in the output intensity of the light source means.

26. The optical sensor as set forth in claim 25 further comprising means for modulating the two distinct wavelengths of light produced by the light source means to sequentially transmit the two distinct wavelengths of light through the single optical fiber on a time-shared basis.

27. The optical sensor as set forth in claim 26 wherein the light source means comprise first and second light emitting diodes, the first light emitting diode providing light having a wavelength of about 565 nm, and the second light emitting diode providing light having a wavelength of about 635 nm.

28. The optical sensor as set forth in claim 25 wherein the light source means further comprise a beam splitter for providing the same light including light at the two distinct wavelengths to both the reference detecting means and the sample detecting means via the sensor probe.

29. The optical sensor as set forth in claim 24 wherein the means for combining comprises a signal processing system operable for taking a ratio of the measurements of the optical characteristics of the thin sensing film at each of the two distinct wavelengths of light in order to provide the self-calibrated measurement.

30. The optical sensor as set forth in claim 24 wherein the thin sensing film is based on the immobilization of Congo Red in a porous polymer film.

31. A dual wavelength optical sensor for measuring chemical properties of a particular quantity comprising:
   a sensor probe including a thin sensing film whose optical characteristics are responsive to the chemical properties of the quantity at at least two distinct wavelengths of light in such a way that when the responses to the at least two distinct wavelengths are combined, a self-calibrated measurement of the measured chemical properties is provided;
   a wide spectrum light source generating multiple wavelength light over a wide spectral range, the at least two distinct wavelengths of light being included in said wide spectral range;
   a single optical fiber for carrying the light from the light source to the sensor probe;
   sample detecting means receiving the light from the sensor probe after it has passed to and from the thin sensing film, the sample detecting means filtering the at least two distinct wavelengths of light from the multiple wavelength light to produce light intensity readings at the respective wavelengths of light; and
   output means for combining the light intensity readings from the sample detecting means to produce the self-calibrated measurement which accounts for changes in the optical characteristics of the thin sensing film that otherwise contribute to instability in the sensor response.

32. The optical sensor as set forth in claim 31 further comprising reference detecting means coupled to the light source in such a way that it monitors the output intensity of the light source to provide compensation to the readings produced by the sample detecting means with respect to spectral variances in the output intensity of the light source.

33. The optical sensor as set forth in claim 32 wherein the output means comprises a signal processing system operable for taking a ratio of the light intensity readings produced by the sample detecting means to provide a self-calibrated output which accounts for both changes in the optical characteristics of the thin sensing film that otherwise contribute to instability in the sensor response and for spectral variances in the output intensity of the light source.

34. The optical sensor as set forth in claim 31 wherein the thin sensing film is based on the immobilization of Congo Red in a porous polymer film.

* * * * *